US012565708B2

(12) United States Patent
Banat et al.

(10) Patent No.: US 12,565,708 B2
(45) Date of Patent: Mar. 3, 2026

(54) COMPOSITE CATALYST WITH MOLYBDENUM MXENE FOR ELECTROCHEMICAL HYDROGENATION OF 2-METHYLFURAN

(71) Applicant: Khalifa University of Science and Technology, Abu Dhabi (AE)

(72) Inventors: Fawzi Banat, Abu Dhabi (AE); Muhammad Ashraf Sabri, Abu Dhabi (AE); Mohammad Abu Haija, Abu Dhabi (AE); Hanifa Taher Alblooshi, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 0 days.

(21) Appl. No.: 18/793,268

(22) Filed: Aug. 2, 2024

(65) Prior Publication Data

US 2026/0035813 A1 Feb. 5, 2026

(51) Int. Cl.

| | |
|---|---|
| *C25B 11/075* | (2021.01) |
| *B01J 27/22* | (2006.01) |
| *C07D 307/36* | (2006.01) |
| *C25B 3/05* | (2021.01) |
| *C25B 3/07* | (2021.01) |

(Continued)

(52) U.S. Cl.
CPC ............. *C25B 11/075* (2021.01); *B01J 27/22* (2013.01); *C07D 307/36* (2013.01); *C25B 3/05* (2021.01); *C25B 3/07* (2021.01); *C25B 11/054* (2021.01); *C25B 11/067* (2021.01)

(58) Field of Classification Search
CPC ............................... B01J 27/22; C25B 11/075
See application file for complete search history.

(56) References Cited

U.S. PATENT DOCUMENTS

2021/0283592 A1* 9/2021 Jiang ................... B01J 37/0213

OTHER PUBLICATIONS

Dong, J.; Zhang, Y.;Hussain, M.I.; Zhou, W.; Chen, Y.;Wang, L.-N. g-C3N4: Properties, Pore Modifications, and Photocatalytic Nanomaterials 2022, 12, 121 (Year: 2022).*

(Continued)

*Primary Examiner* — Matthew E. Hoban
(74) *Attorney, Agent, or Firm* — Billion & Armitage

(57) ABSTRACT

A composite catalyst for electrochemical hydrogenation (ECH) of furfural (FF) to 2-methylfuran (MF) includes Molybdenum Mxene and carbon nitride. In an example, the composite catalyst is two dimensional (2D)-on-2D $Mo_3C_2@g\text{-}C_3N_4$. By performing the ECH of FF with the composite catalyst in a mild electrolyte solution and enabling the selective production of MF at particular applied potentials, the composite catalyst minimizes challenges commonly associated with conventional ECH methods. The structure of the composite catalyst, in which Molybdenum sites act as active centers and nitrogen facilitates the hydrogenation of FF, enables direct hydrogenation of FF to MF, thereby increasing selectivity and efficiency. The composite catalyst shows a high preference for FF reduction over HER, significantly increasing the faradaic efficiency (FE). The Molybdenum Mxene can be Molybdenum carbide. In an example, an amount of Molybdenum Carbide in the composite catalyst is between about 5 and about 10 mass percent.

11 Claims, 7 Drawing Sheets

(51) Int. Cl.
C25B 11/054 (2021.01)
C25B 11/067 (2021.01)

(56) References Cited

OTHER PUBLICATIONS

Nasri. Effect of MXene Loaded on g-C3N4 Photocatalyst for the Photocatalytic Degradation of Methylene Blue. Energies 2022, 15, 955. (Year: 2022).*

Bababrik, Reda , et al., "A comparative study of thermal- and electrocatalytic conversion of furfural: methylfuran as a primary and major product", Journal of Applied Electrochemistry, Apr. 29, 2020, 8 pages.

Bharath, G. , et al., "High-Grade Biofuel Synthesis from Paired Electrohydrogenation and Electrooxidation of Furfural Using Symmetric Ru/Reduced Graphene Oxide Electrodes", ACS Appl. Mater. Interfaces 2021, 13, 24643-24653.

Jung, Sungyup , et al., "Enhanced activity for electrochemical hydrogenation and hydrogenolysis of furfural to biofuel using electrodeposited Cu catalysts", Catalysis Today 323 (2019) 26-34.

Li, Xinxin , et al., "Strategies for controlling gas evolution reactions to boost the divergent paired electrochemical upgrading of furfural in acidic environment", Chemical Engineering Journal 470 (2023) 144093.

May, Andrew S., et al., "Kinetics of furfural electrochemical hydrogenation and hydrogenolysis in acidic media on copper", React. Chem. Eng., 2021, 6, 2075.

May, Andrew S., et al., "Modeling Competing Kinetics between Electrochemical Reduction of Furfural on Copper and Homogeneous Side Reactions in Acid", Energy Fuels 2022, 36, 11001-11011.

Munirathinam, Balakrishnan , et al., "Recent Advances in Metallic Catalyst Materials for Electrochemical Upgrading of Furfurals to Drop-in Biofuels: A Mini Review", Energy Technol. 2023, 11, 2300307, 13 pages.

Nilges, Peter , et al., "Electrochemistry for biofuel generation: production of furans by electrocatalytic hydrogenation of furfurals", Energy Environ. Sci., 2013, 6, 2925.

Richel, Aurore , et al., "Recent advances in continuous reduction of furfural to added value chemicals", Current Opinion in Green and Sustainable Chemistry 2022, 37, 5 pages.

Sabri, Muhammad Ashraf, et al., "Highly efficient PdNiB decorated over carbon supports for the electrochemical valorization of furfural and 5-hydroxymethylfurfural into fuels", Fuel 353 (2023) 129241, 15 pages.

Zhang, Lijuan , et al., "A review of thermal catalytic and electrochemical hydrogenation approaches for converting biomass-derived compounds to high-value chemicals and fuels", Fuel Processing Technology 226 (2022) 107097.

Zhou, Peng , et al., "Electrochemical Hydrogenation of Furfural in Aqueous Acetic Acid Media with Enhanced 2-Methylfuran Selectivity Using CuPd Bimetallic Catalysts", Angew. Chem. Int. Ed. 2022, 61.

Zhou, Peng , et al., "Selective electrochemical hydrogenation of furfural to 2-methylfuran over a single atom Cu catalyst under mild pH conditions", Green Chem., 2021, 23, 3028.

* cited by examiner

100 ⟍

| Making or obtaining Mo Mxene | 102 |

↓

| Mixing urea, melamine, and Mo Mxene | 104 |

↓

| Heating the mixture to form a composite of Mo Mxene and cabon nitride | 106 |

↓

| Grinding the composite into a powder | 108 |

102

102A — Mixing MAX phase Molybdenum aluminum carbide with HCl solution

102B — Processing the mixture hydrothermally to form multi-layered 2D Mxene

102C — Washing and drying the Mo Mxene

200

202 — Using a Molybdenum Mxene catalyst in an electrochemical reactor to convert FF to MF 204 — Removing the converted MF from the electrochemical reactor

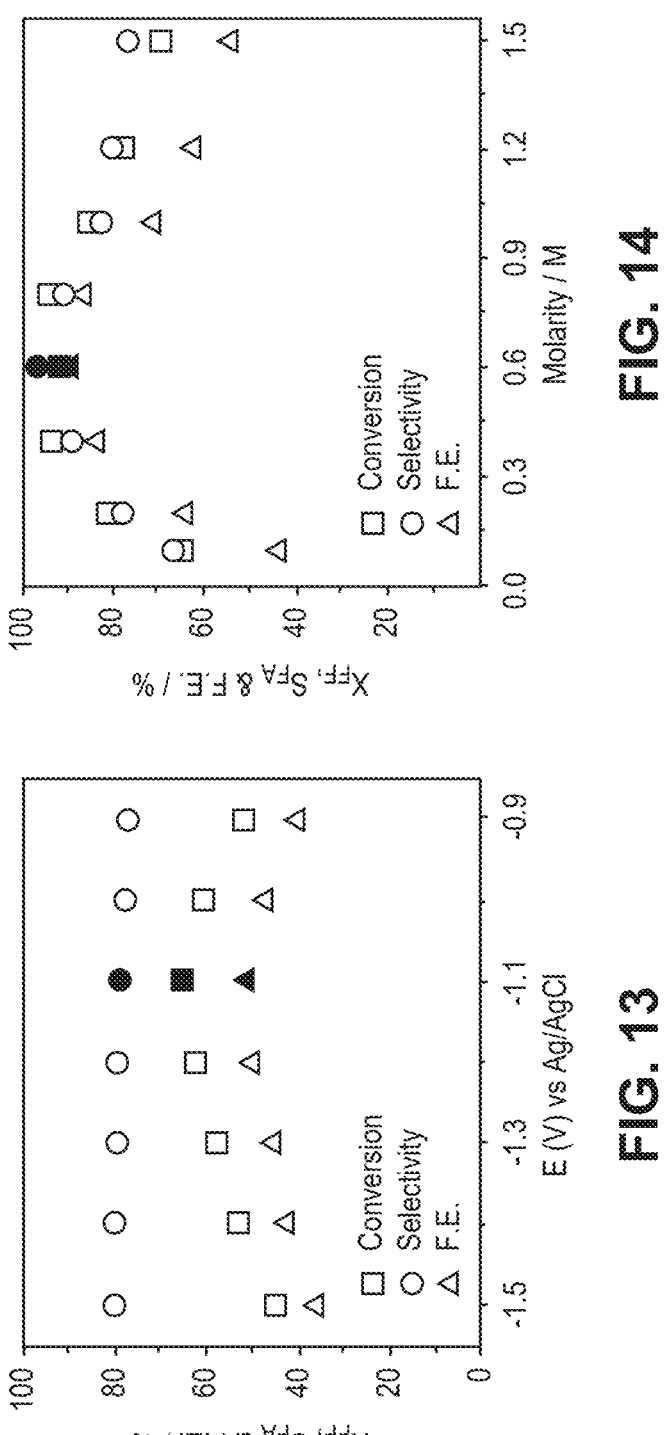

COMPOSITE CATALYST WITH MOLYBDENUM MXENE FOR ELECTROCHEMICAL HYDROGENATION OF 2-METHYLFURAN

TECHNICAL FIELD

The subject matter disclosed herein relates to a composite catalyst and, in particular, to a Molybdenum Mxene catalyst for electrochemical hydrogenation.

BACKGROUND

The bio-refinery industry recognizes furfural (FF) as a promising bio-based feedstock that is central to the production of value-added chemicals such as furfuryl alcohol (FA) and 2-methylfuran (MF). The growing global pharmaceutical market, which is expected to grow at a steady rate of over 4-5% in the coming years, also offers a number of promising opportunities for the use of MF. For example, MF is a key ingredient in the synthesis of several drugs, including atropine, sodium acetate, furadantine, anisodamine, and thiamine furan. One notable application of MF is its use in the synthesis of vitamin B1, a pivotal nutrient. MF is also used as a diagnostic tool for lung cancer screening and in the production of the anti-malarial drug chloroquine. In addition, MF is a key component in the production of methyl furfural, aliphatic compounds and sulfur and nitrogen heterocycles. The versatility and widespread potential of MF is also demonstrated by its use as an intermediate in the synthesis of pesticides, flavorings, and fragrances. Given this wide range of applications, the market for MF is expected to continue to grow.

Electrochemical hydrogenation (ECH) can be used to convert furfural (FF) to 2-methylfuran (MF). Existing catalysts for ECH of FF to MF, such as, for example, copper or ruthenium catalysts, have several drawbacks. First and foremost, these catalysts have difficulty achieving high faradaic efficiency (FE) and selectivity for MF. This is largely due to competing reactions, such as hydrogen evolution reactions (HER), which hinder the efficient and sustainable conversion of FF. As a result, the performance of these catalysts is inadequate in terms of both efficiency and selectivity.

It would be beneficial to develop an improved catalyst for ECH with high FE and high selectively, which also facilitates direct conversion of FF to MF.

SUMMARY

According to one aspect, a catalyst for electrochemical hydrogenation (ECH) of furfural to 2-methylfuran includes a two-dimensional (2D) multi-layered Molybdenum Mxene and a two-dimensional (2D) carbon nitride nanosheet. The 2D multi-layered Molybdenum Mxene is dispersed on a surface of the 2D carbon nitride nanosheet.

According to another aspect, a method of making an electrocatalyst for use in electrochemical hydrogenation (ECH) of furfural to 2-methylfuran includes mixing urea, melamine and Molybdenum Mxene to form a mixture. The method further includes heating the mixture to form a two-dimensional (2D)-on-2D composite of Molybdenum Mxene and carbon nitride, and then forming the composite into an electrocatalyst powder.

According to another aspect, a method of producing 2-methylfuran (MF) using a composite catalyst includes directly converting furfural to 2-methylfuran (MF) using an electrochemical reactor and a composite catalyst of 2D Molybdenum Mxene on a carbon nitride nanosheet. The method further includes removing the converted MF from the electrochemical reactor. The composite catalyst has a high selectivity and preference for furfural reduction over a hydrogen evolution reaction (HER).

This summary is intended to provide an overview of subject matter of the present disclosure. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed herein.

FIG. 13 is a plot of conversion, selectivity and faradaic efficiency (FE) for a sample of composite catalyst as a function of applied potential.

FIG. 14 is a plot of conversion, selectivity and FE for the sample of FIG. 13 as a function of molarity.

DETAILED DESCRIPTION

Figures 1, 2:
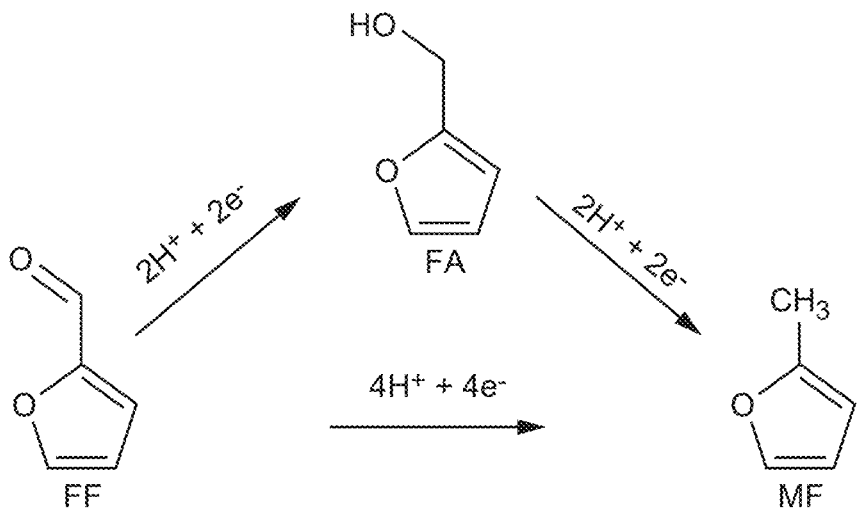
FIG. 1 is a schematic of the chemical pathways for furfural (FF) to 2-methylfuran (MF).
FIG. 2 is a flowchart illustrating a process for making a composite catalyst of Molybdenum Mxene and carbon nitride.

The present disclosure is directed to a novel composite catalyst of Molybdenum Mxene and carbon nitride that improves the selective ECH of FF to MF under acidic conditions (pH≤0.7), while attenuating undesirable HER. In some embodiments, the Molybdenum Mxene includes Molybdenum carbide. In some embodiments, the Molybdenum Mxene includes Molybdenum nitride. In some embodiments, the Molybdenum Mxene includes both Molybdenum nitride and Molybdenum carbide in combination. MXenes are compounds derived from the carbides or nitrides of the MAX phases. These Molybdenum MXenes exist in diverse forms, including, for example, $Mo_3C_2$, $Mo_2C$, $MO_2N$, $Mo_5N_6$.

In some embodiments, the Molybdenum Mxene is on a graphitic carbon nitride ($g$-$C_3N_4$) nanosheet/support to form the composite catalyst. The composite catalyst can be $Mo_3C_2@g$-$C_3N_4$. In some embodiments, the Molybdenum Mxene is in the form of multilayered sheets and thus the composite catalyst is two dimensional (2D)-on-2D $Mo_3C_2@g$-$C_3N_4$.

The composite catalyst can be prepared by an environmentally friendly method by synthesizing MXene from the MAX phase—for example, molybdenum aluminum carbide ($Mo_3AlC_2$, 99%)—using hydrochloric acid (HCl) instead of the commonly used hydrofluoric acid (HF), which is a toxic chemical. Incorporating molybdenum (Mo) into the catalyst composition is of strategic importance for enhancing the corrosion resistance of the composite catalyst, particularly in acidic environments where the ECH of FF is conducted. This leads to more durable and efficient catalysts.

The composite catalyst facilitates direct conversion of FF into MF, bypassing the usual intermediate stage of FA, which significantly increases the selectivity for MF production. In addition, a conceptual continuous system for MF production is introduced to improve operational efficiency and product separation from the electrochemical reactor. This highlights the potential of the $Mo_3C_2@g$-$C_3N_4$ composite or composite catalyst as an efficient catalyst for biomass valorization, resulting in a remarkable advance in the field of biomass conversion and the development of sustainable materials.

The composite catalyst is also positioned to capitalize on growth in other industries that rely on catalytic processes, such as chemical manufacturing and pharmaceuticals. Among the current electrocatalytic options, the composite catalyst stands out with its superior performance, ease of manufacture and favorable properties. Potential applications for the composite catalyst include industries, such as biorefineries, where efficiency, cost effectiveness and reliability in catalytic processes are paramount.

The composite catalyst has high faradaic efficiencies (FE) of over 90% for MF at mild electrolyte concentrations ($0.1 \leq$ molar sulfuric acid$\leq 0.6$) and at applied potentials of $-1.1$ V versus a saturated Ag/AgCl electrode. The structure of the composite catalyst, in which Mo sites act as active centers and nitrogen facilitates the hydrogenation of FF, supports the direct hydrogenation of FF to MF, which significantly increases selectivity and efficiency. The composite catalyst shows a high preference for FF reduction over HER, significantly increasing the faradaic efficiency of ECH reactions by suppressing the competing HER.

FIG. 1 shows the ECH pathways for furfural (FF) to methyl-furan (MF). Furfural can be converted to MF via an intermediate stage that produces furfural alcohol (FA) (e/FF=2) from MF, and then FA is converted to MF. Reactions (1) and (2) for conversion via an intermediate reaction are shown below:

$$FF+2H^++2e^- \rightarrow FA \qquad (1)$$

$$FA+2H^++2e^- \rightarrow MF+H_2O \qquad (2)$$

Furfural can also be directly converted to MF(e$^-$/FF=4) via Reaction 3 below:

$$FF+4H^++4e^- \rightarrow MF+H_2O \qquad (3)$$

The composite catalyst enables direct conversion of FF to MF. By performing the ECH of FF with the composite catalyst in a mild electrolyte solution and enabling the selective production of MF at certain applied potentials, the composite catalyst minimizes the operational challenges associated with conventional ECH methods. Using the composite catalyst for selective ECH of FF to MF under mild conditions results in efficient and sustainable FF production, which can be used, for example, for the bio-refinery industry.

FIG. 2 is a flowchart for a process 100 for making a composite catalyst of Molybdenum Mxene and carbon nitride. The process 100 includes, at step 102, making or obtaining Molybdenum Mxene. (See FIG. 3 for sub-steps under step 102.) At step 104, the process 100 includes mixing urea, melamine and Molybdenum Mxene to form a uniform mixture. In some embodiments, a molar ratio of urea to melamine is about 1:1. In other embodiments, a higher or lower molar ratio can be used.

The amount of Molybdenum Mxene used in the mixture can vary. In some embodiments, a mass of Molybdenum Mxene in the mixture is between about 2 and about 12 percent. In some embodiments, the mass of Molybdenum Mxene in the mixture is between about 4 and about 9 percent. In other embodiments, the mass of Molybdenum Mxene in the mixture is between about 5 and about 8 percent. In other embodiments, the mass of Molybdenum Mxene in the mixture is about 7 percent. As used herein, the amount of Molybdenum Mxene in the composite catalyst (formed through the process 100 of FIG. 2) correlates to the mass percent of Molybdenum Mxene used in step 104.

As step 104 is described above, the Mxene is mixed with the materials used in forming the graphitic carbon nitride (GN). Thus, the process 100 includes creating the 2D on 2D structure as the GN is also formed. In other embodiments, Mxene may be combined with already formed GN to create the 2D on 2D structure.

Next, step 106 includes heating the mixture to form a composite of Molybdenum Mxene and carbon nitride. The mixture is placed in a furnace and the temperature in the furnace is incrementally increased and then held at the maximum temperature for a predetermined time. In some embodiments, the maximum temperature is between about 800 and 830 K. In some embodiments, the mixture is held at the maximum temperature for about 3 to about 5 hours. In some embodiments, the mixture is held at the maximum temperature for about 4 hours. The temperature in the furnace is then incrementally decreased. At step 108, the composite can be ground into a fine powder that can be used as an electrocatalyst.

The composite catalyst resulting from the process 100 of FIG. 2 is a layered structure of graphitic carbon nitride nanosheets with nanoscale 2D multilayered Molybdenum Mxene sheets embedded on the surface of the graphitic carbon nitride. The dispersed nanosheet-like configuration of the composite/catalyst is favorable for the uptake of 2D Mxene on the surface.

Figure 3:
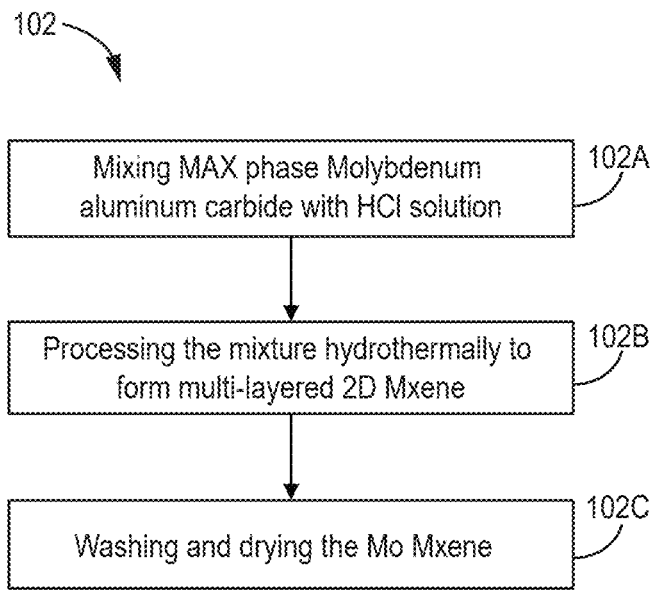
FIG. 3 is a flowchart illustrating a process for making Molybdenum Mxene.

FIG. 3 is a flowchart for substeps under step 102 of the process 100 of FIG. 2 for making Molybdenum Mxene. It is noted that sub-steps 102A-102C are optional and are not applicable if the Molybdenum Mxene is purchased, or otherwise obtained in its intended form, for use in step 104.

At sub-step 102A, MAX Phase Molybdenum aluminum carbide is mixed with a solution of hydrogen chloride (HCl) and then stirred for a predetermined period-such as, for example, an hour. At sub-step 102B, the mixture undergoes hydrothermal processing at an elevated temperature and pressure. Sub-step 102B results in etching of the aluminum and formation of a two dimensional (2D) multilayered Mxene. At sub-step 102C, the resulting Mxene undergoes multiple washes with water, followed by rinsing with ethanol, and then drying overnight. In some embodiments, the mixture is dried at an elevated temperature (for example, about 383 K).

Figure 4:
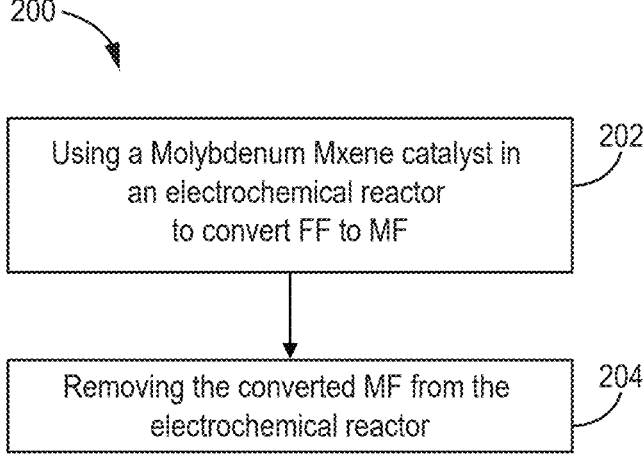
FIG. 4 is a flowchart illustrating a process for producing 2-methylfuran (MF).

FIG. 4 is a flowchart of a process 200 for producing 2-methylfuran (MF). At step 202, an electrochemical reactor is used in conjunction with the composite catalyst described herein to convert FF to MF. The composite catalyst facilitates direct conversion of FF to MF and has high selectivity such that the catalyst suppresses the competing HER.

At step 204, the converted MF is removed from the electrochemical reactor. In some embodiments, the electrochemical reactor is operated at a temperature of about 63° C., as this corresponds to the boiling point of MF and enables the vaporization of MF as it is formed in the electrochemical reactor. In some embodiments step 304 includes using a condenser on top of the electrochemical reactor to collect the vaporized MF and facilitate its continuous separation. In some embodiments, the process 200 may include additional steps after step 304 for post processing of the MF.

In some embodiments, the process 200 is operated continuously such that the MF is removed from the reactor and captured as it is formed. Maintaining the process at about 63° C. creates a self-propelling reaction environment in which MF is immediately vaporized and captured as it is formed, thereby preventing the MF from re-entering into the reaction mixture. This facilitates an environment in the reaction chamber that continuously drives the reaction to form MF. The process 200 can thus include a continuous, self-sustaining system that minimizes the manual intervention required for product extraction and potentially improves the overall efficiency and sustainability of the process.

Systematic experiments, including those provided in the Examples below, demonstrate that the composite catalyst disclosed herein exhibits high activity and selectivity and suppresses the hydrogen evolution reaction (HER), thereby facilitating efficient furfural (FF) conversion. The structural uniqueness of the composite catalyst is emphasized by its two-dimensional nanosheet configuration, which enables effective distribution of $Mo_3C_2$ multilayered nanosheets on the $g$-$C_3N_4$ nanosheet surfaces, significantly improving the ECH process. The unique configuration of the catalyst is crucial for achieving high selectivity for 2-methylfuran (MF) under mild acidic conditions.

The experiments included testing various samples of the composite catalyst having different amounts of Mxene ($Mo_3C_2$). Among the various compositions tested, $Mo_3C_2$@$g$-$C_3N_4$ with a mass fraction of 7% $Mo_3C_2$ proved to be particularly effective for the direct conversion of FF to MF. This particular composite significantly suppressed HER, resulting in high product yield or selectivity and high faradaic efficiency. The enhanced performance of this composite was confirmed by laboratory scale tests and resulted in FF conversion of about 92%, MF selectivity of up to 97% and faradaic efficiency (FE) of 90% under optimized conditions. (See Example 5 and FIG. 14 under the Examples section below.) This represents a significant improvement compared to previous studies of other catalysts in which the faradaic efficiency and selectivity for MF was considerably lower by comparison. In the context of the electrochemical conversion of FF to MF, a notable drawback of existing catalysts is that they are unable to achieve high faradaic efficiency and MF yield simultaneously. This limitation often results from the reduced performance, especially in faradaic efficiency, caused by the formation of by-products and the hydrogen evolution reaction (HER). The composite catalyst provided herein enables high conversion of FF to MF under ambient conditions, combining cost-effectiveness with high performance through an electrochemical process.

The composite catalyst, consisting only of Molybdenum (Mo), Nitrogen (N) and carbon (C), offers similar or improved results to existing catalysts, but at much lower sulfuric acid concentrations (0.1-0.5 M), reducing both manufacturing and operating costs. In contrast, existing catalysts commonly use expensive raw materials, such as, for example, ruthenium.

The composite catalyst disclosed herein is characterized by a well-developed porous structure. In some embodiments, the surface area of the composite catalyst is about 25 to about 32 $m^2$/g. In some embodiments, the surface area is about 29 $m^2$/g. In some embodiments, an average pore size of the composite catalyst is between about 2 and about 6 nm. In some embodiments, the average pore size is between about 2.8 and about 5.2 nm. The Brunauer-Emmett-Teller (BET) and Barrett-Joyner-Halenda (BJH) equation models with a surface area analyzer (3Flex, Micromeritics, USA) using the N2 adsorption-desorption isotherm at 77 K were used to determine the surface area (SA) and pore size distribution (PSD).

The porosity described herein is the porosity of the composite catalyst overall, which is a combination of Mxene nanosheets on carbon nitride nanosheets (2D on 2D). Both carbon nitride and Mxene are porous. Typically, the porosity of graphitic carbon nitride (GN) nanosheets is higher than that of MXene nanosheets when evaluated independently. As a result, based on the prepared catalysts and materials, the porosity of the composite catalyst (MXene on GN) can generally be expected to be between the separate porosities of carbon nitride nanosheets and MXene nanosheets.

The composite catalyst has a thermal stability of up to about 330-350° C., which enables versatile use at higher temperatures. Thermogravimetric analysis of the composite catalyst is included below in the Examples.

The composite catalyst was developed for the electrochemical conversion of FF to MF by hydrodeoxygenation. It exhibits high catalytic activity and stability even at room temperature, coupled with excellent selectivity (≥90%) and high faradaic efficiency (≥90%) in the production of MF, as well as remarkable reusability. The composite catalyst is particularly efficient for hydrodeoxygenation processes at room temperature.

In some embodiments, the furfural conversion of the composite catalyst is at least 60 percent. In some embodiments, the furfural conversion is at least 70 percent, at least 80 percent or at least 90 percent. In some embodiments, the faradaic efficiency (FE) of the composite catalyst is at least 90 percent.

Electrochemical experiments have shown that factors, such as the applied potential and the electrolyte concentration, are important parameters for optimizing the conversion efficiency, faradaic efficiency, and selectivity to MF. An observed non-linear trend in these parameters indicates an optimal operating range and emphasizes the careful design of the composite catalyst to address common challenges such as the HER and side reactions in FF conversion. This is shown in the Examples below.

The following Examples are intended to illustrate the above invention and should not be construed as to narrow its scope. One skilled in the art will readily recognize that the inventors suggest many other ways in which the invention could be practiced. It should be understood that numerous variations and modifications may be made while remaining within the scope of the invention.

EXAMPLES

Materials

Furfural (99%), urea (urea ($NH_2CONH_2$, ≥99%), acetonitrile (99.8%), melamine (empirical formula, $C_3H_6N_6$, 99%), and sulfuric acid ($H_2SO_4$, 99%) were obtained from Sigma-Aldrich and used without further purification.

Carbon black (CB, >99.9%, SA: 75 $m^2$/g) and MAX-Phase Molybdenum Aluminum Carbide ($Mo_3AlC_2$, 99%) were obtained from Alfa Aesar and Luoyang Tongrun Info Technology Co., Ltd., respectively, and used without further purification.

Deionized water (DIW) from Milli-Q Plus (Merck Millipore Co., Germany) was used in the experimental procedures.

Example 1—MXene ($Mo_3C_2$) Synthesis

Figures 5, 6:
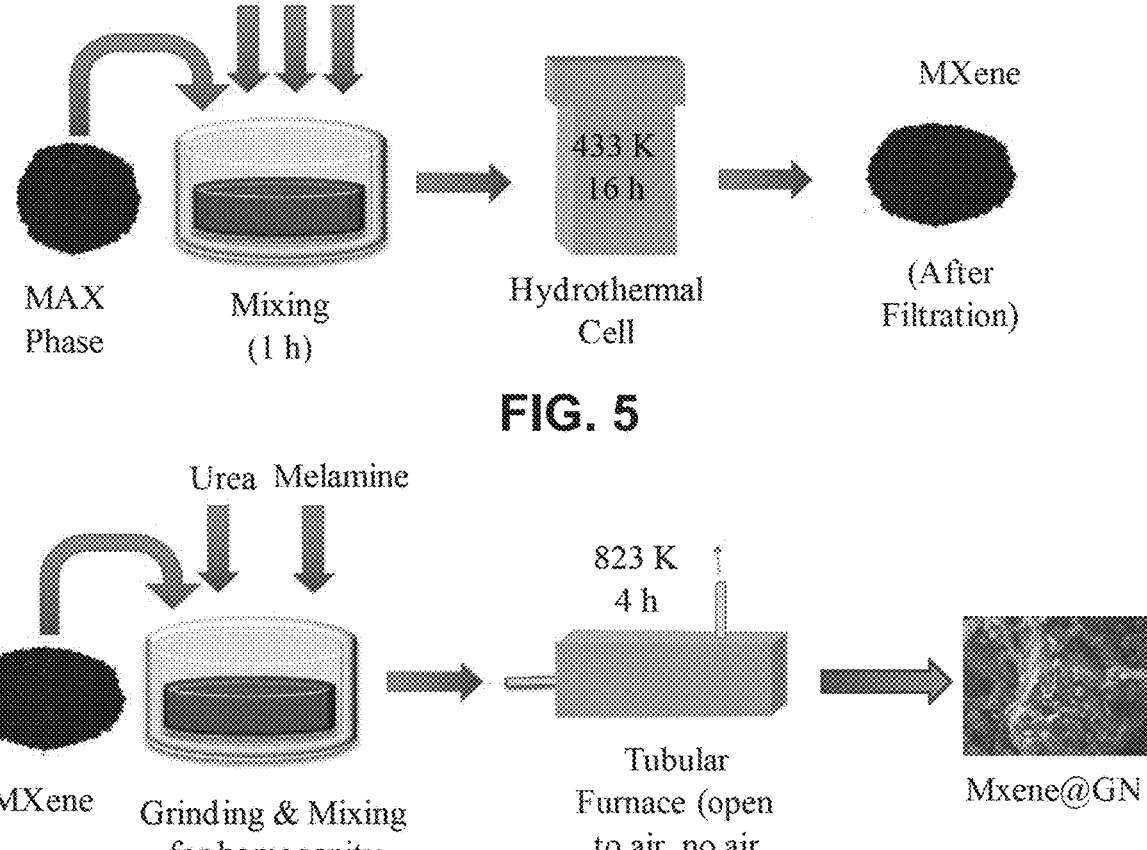
FIG. 5 is a schematic illustrating the steps in making Molybdenum Mxene.
FIG. 6 is a schematic illustrating the steps in making the composite catalyst.

A Molybdenum MXene, specifically ($Mo_3C_2$), was synthesized through a hydrothermal method, eliminating the need for hydrofluoric acid (HF). FIG. 5 illustrates the synthesis of $Mo_3C_2$ schematically.

One gram of the MAX phase (molybdenum aluminum carbide) was introduced into 30 mL of HCl solution (various samples were prepared at 1 M, 3 M, and 6 M), for use as an etching agent, and the mixture was stirred continuously using a magnetic stirrer (Premium Hotplate Stirrer, Daihan Scientific Co. Ltd, Model: SMHS-6) for an hour. Following this, the mixture was transferred into a hydrothermal cell, which was then placed at 433 K for 16 hours. The elevated pressure and temperature within the hydrothermal cell facilitated the etching of aluminum, culminating in the formation of 2D multilayered MXenes ($Mo_3C_2$). (The temperature inside the hydrothermal cell was above the boiling point of water, thus creating vapors and increased pressure inside the cell.) The resulting MXene ($Mo_3C_2$), labeled MX, underwent a washing process. The MXene was manually mixed with deionized water (DIW) and then filtered. This was repeated several times, after which the MXene was rinsed with ethanol. After washing, the $Mo_3C_2$ mixture (MX) was dried overnight at a temperature of 383 K and subsequently stored in glass vials.

Example 2—MXene/g-$C_3N_4$ Synthesis During g-$C_3N_4$ Synthesis to Form the Composite Catalyst (2D-on-2D $Mo_3C_2$@g-$C_3N_4$)

FIG. 6 illustrates the synthesis of the composite catalyst (2D-on-2D $Mo_3C_2$@g-$C_3N_4$). The composite catalyst was synthesized in a manner that incorporated MX during the graphitic carbon nitride (GN) formation process. Different composite catalyst samples were formed with varying amounts of MX in the composite catalyst to evaluate the impact of the MX amount on catalyst performance.

To form the composite catalyst, 9 g of urea, 18.92 g of melamine, and a variable amount of MX were thoroughly mixed (manually with a mortar and pestle) to attain a uniform mixture. A molar ratio of 1:1 urea to melamine was used. The results revealed that the conversion yield of GN from urea to melamine was approximately 30%, inferring that a mass of approximately 8.37 g of GN was generated from 9 g of urea and 18.92 g of melamine.

The mixture was then transferred to a crucible, which was tightly enveloped with aluminum sheeting, encompassing six layers. Thereafter, the crucible was placed within a horizontal tubular furnace exposed to the surrounding atmosphere. The temperature of the furnace was gradually increased at a rate of 2.5 K/min from room temperature to 823 K. Upon reaching 823 K, the temperature was maintained for a span of 4 hours, after which it was reduced back to room temperature at a decreasing rate of 2.5 K/min. The resultant MXene/GN composite was then ground into a fine powder to be used as an electrocatalyst.

The samples had varying quantities of MX that were mixed with the urea and melamine. The amount of GN in the samples was determined by the yield provided above. Table 1 below shows the amounts of MX and GN in each sample and the corresponding percent of MX. The MX/GN composite catalysts evaluated had MX mass ratios of 1%, 3%, 5%, 7%, and 10% within the composite catalyst. The specimens were labeled MGCX, where 'X' denotes the mass percentage of MX in the composite catalyst. For instance, MGC7 is a composite catalyst composed of MX and GN and synthesized via this in situ method, and MGC7 has an MX mass percentage of 7 and a GN mass percentage of 93.

TABLE 1

| Variable quantities of Mxene used in synthesis of composite catalyst samples | | | |
|---|---|---|---|
| Sample | GN (g) | MX (g) | Mass Percent (% ) |
| 1 (MGC1) | 8.37 | 0.09 | 1.06 |
| 2 (MGC3) | 8.37 | 0.26 | 3.01 |
| 3 (MGC5) | 8.37 | 0.44 | 4.99 |
| 4 (MCG7) | 8.37 | 0.63 | 7.00 |
| 5 (MCG10) | 8.37 | 0.93 | 10.0 |

Example 3—Morphological and Structural Characteristics

Figure 7C:
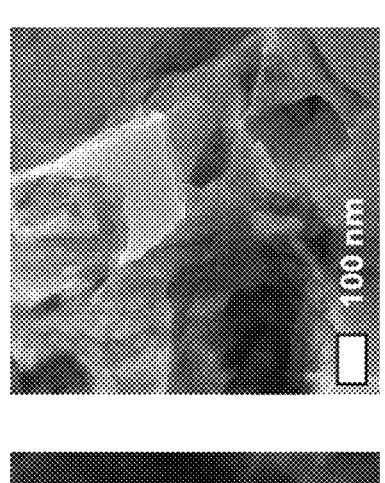
FIG. 7C is another TEM image of the composite sample of FIG. 7A.
Figure 7B:
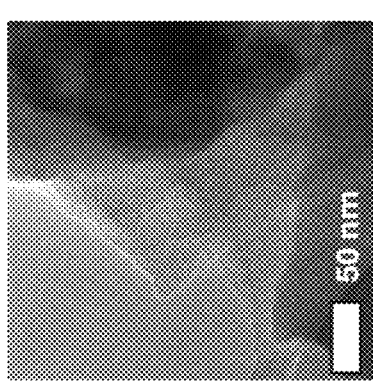
FIG. 7B is a transmission electron microscope (TEM) image of the composite catalyst sample of FIG. 7A.
Figure 7A:
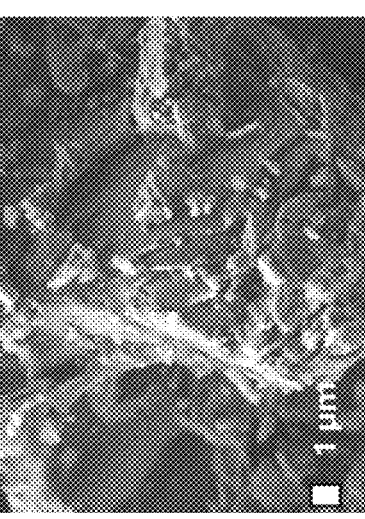
FIG. 7A is a scanning electron microscope (SEM) image of a sample of the composite catalyst.

FIG. 7A shows a scanning electron microscope (SEM) image of the MCG7 sample of Table 1. FIG. 7A illustrates the layered structure of the GN with the MX multilayered sheets embedded on the sample surface.

FIGS. 7B and 7C show transmission electron microscope (TEM) images of the composite catalyst sample (MCG7) of FIG. 7A at two different resolutions. As shown in FIGS. 7B and 7C, a 2D structure of the dispersed nanosheet type is recognizable, with the stacked layers clearly discernible. This dispersed nanosheet-like configuration of the catalyst is favorable for the uptake of 2D MX on the surface. Furthermore, the images show that the nanoscale 2D multilayered MX sheets are well dispersed, with no recognizable area of agglomeration.

Figures 8A, 8B, 8C, 9, 10:
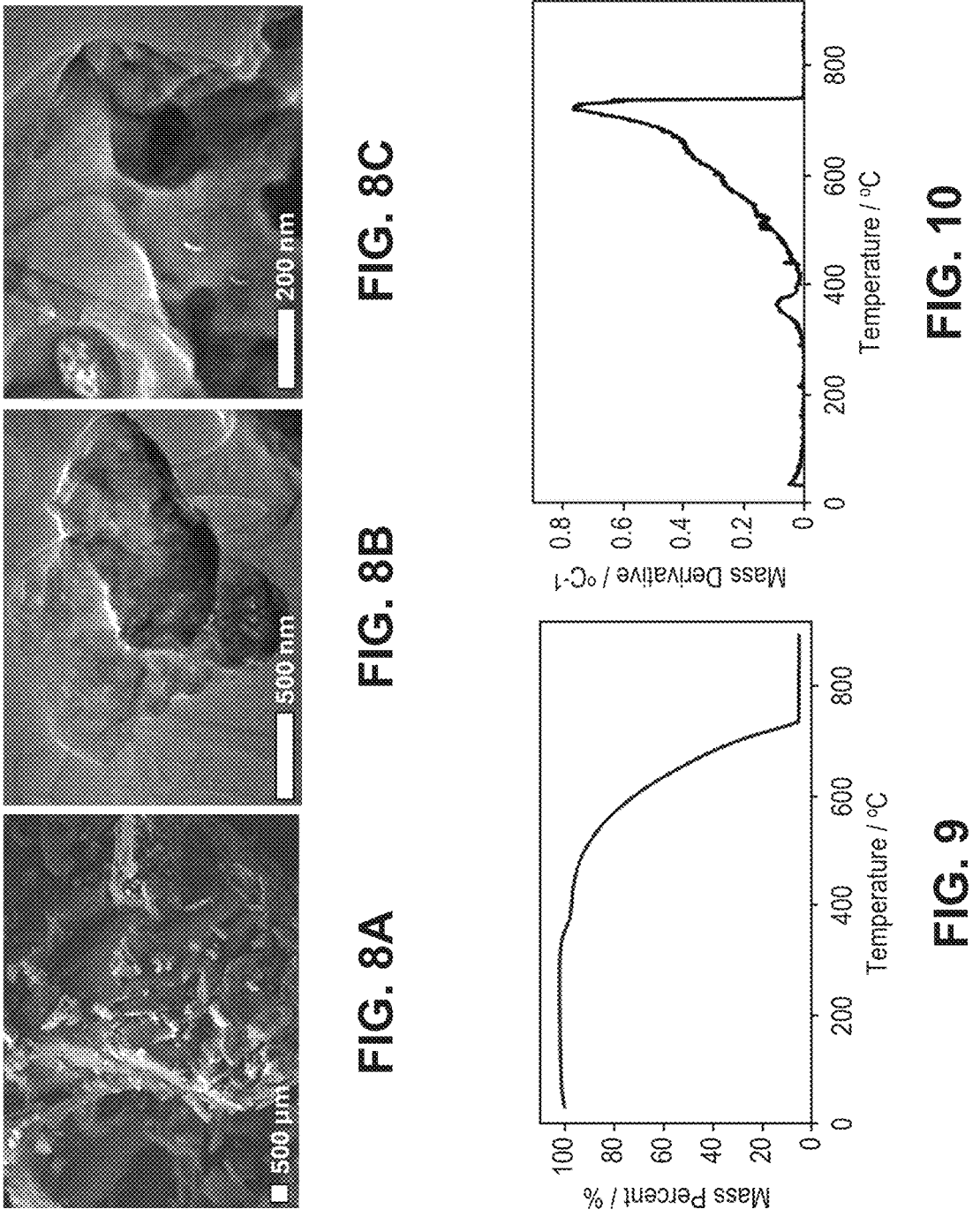
FIG. 8A is a scanning electron microscope (SEM) image of another sample of the composite catalyst.
FIG. 8B is a transmission electron microscope (TEM) image of the composite catalyst sample of FIG. 8A.
FIG. 8C is another TEM image of the composite sample of FIG. 8A.
FIG. 9 is a plot of mass percent of a sample of the composite catalyst as a function of temperature under thermogravimetric analysis (TGA).
FIG. 10 is a plot of a rate of mass loss of the sample as a function of temperature under differential thermogravimetric analysis (DTGA).

FIG. 8A shows a scanning electron microscope (SEM) image of the MCG10 sample of Table 1. FIG. 8A illustrates the layered structure of the GN with the MX sheets embedded on the sample surface.

FIGS. 8A and 8B show transmission electron microscope (TEM) images of the composite catalyst sample of FIG. 8A (MCG10) at two different resolutions. As shown in FIGS. 8B and 8C, and like FIGS. 7B and 7C for the MCG7 sample, a 2D structure of the dispersed nanosheet type is recognizable and the sheets are well dispersed.

Example 3—Thermal Stability of Composite Catalyst

FIG. 9 shows the thermogravimetric analysis (TGA) of the MCG7 sample of Table 1. The TGA curve shows the mass percent of the sample as a function of temperature. Initially, the sample maintains a mass close to 100% at temperatures up to about 350° C., indicating thermal stability in this range. A slight mass loss is observed between 350° C. and 400° C. A significant mass loss occurs between 400° C. and 750° C., with the most pronounced decomposition starting around 500° C. and ending near 750° C. By 750° C., the mass stabilizes at approximately 5%, indicating the majority of the sample has decomposed, leaving a small residue.

FIG. 10 shows the differential thermogravimetric analysis (DTGA) of the MCG7 sample. The DTGA curve represents the rate of mass loss (%/° C.) as a function of temperature. Two major peaks are observed in FIG. 10, indicating distinct stages of decomposition. The broader peak around 350° C. to 400° C. corresponds to a slower decomposition rate. A significant peak around 600° C. to 750° C. indicates the main decomposition event, with the maximum rate of mass loss occurring around 700° C.

Together, the results of FIGS. 9 and 10 indicate that the composite catalyst undergoes two stages of thermal decomposition, with the primary decomposition phase occurring between 350° C. and 400° C. The composite catalyst is thus thermally stable up to about 340 or about 350° C.

Example 4—Electrode Preparation

Electrodes were prepared by thoroughly mixing 5% PVDF, 5% carbon black, and 90% catalyst, and drop-casting the mixture onto graphite sheets, followed by overnight drying at 333 K. The electrodes were used as working electrodes in a standard three-electrode setup.

The electrodes were made with different catalyst compositions, including the samples of Table 1, to determine the optimum amount of MX used in the composite catalyst. Other control catalysts were also used in the electrodes for comparison-see Table 2 below.

Example 5—Electrochemical Performance

Electrochemical performance evaluation of the electrocatalyst/composite catalyst was performed using a standard three-electrode setup with a Biologic VMP-300 electrochemical workstation. The catalyst electrode was used as a working electrode. A Pt wire and an Ag/AgCl electrode were used as auxiliary and reference electrodes, respectively. The electrolytic medium consisted primarily of sulfuric acid (0.1 M up to 1 M, unless otherwise stated), with acetonitrile serving as co-solvent in experiments with 50 mM furfural (FF).

Subsequent experimentation involved studying furfural conversion under varying parameters such as applied potential and electrolyte molarities (see FIGS. 13 and 14) using an H-cell setup. The conversion process and the resulting products were analyzed using Shimadzu HPLC, which provides information on the conversion efficiency, selectivity and faradaic efficiency. Electrochemical conversion experiments for ECH of FF were performed in an H-Cell configuration with the Nafion membrane acting as a separator between the cathodic and anodic sections. The chronoamperometry (time-dependent current variations at constant applied potential) were investigated to determine the ECH performance of the electrocatalyst/.

Table 2 below shows the furfural conversion efficiency of electrodes made with varies materials and composites. The electrodes are used in an H-cell setup and immersed in 50 mM FF, 100 mM sulfuric acid and 20 vol % acetonitrile.

The initial FF concentration was known and the final FF concentration was determined using HPLC and standard calibration curve prepared for the FF using the HPLC method. Through these concentrations, the initial mass of the FF and the final mass of the FF in the solution was determined, and the conversion was calculated.

TABLE 2

Furfural conversion of electrodes made with different catalyst materials

| Material | Furfural Conversion (%) |
|---|---|
| GN (Graphitic carbon nitride) | 13.2 |
| MAX(MAX phase) | 21.6 |
| MX (MXene) only | 27.9 |
| MGC3 (MX mass ratio of 3%) | 29.8 |
| MGC5 (MX mass ratio of 5%) | 32.4 |
| MGC7 (MX mass ratio of 7%) | 60.2 |
| MGC10 (MX mass ratio of 10%) | 38.2 |

Figure 11:
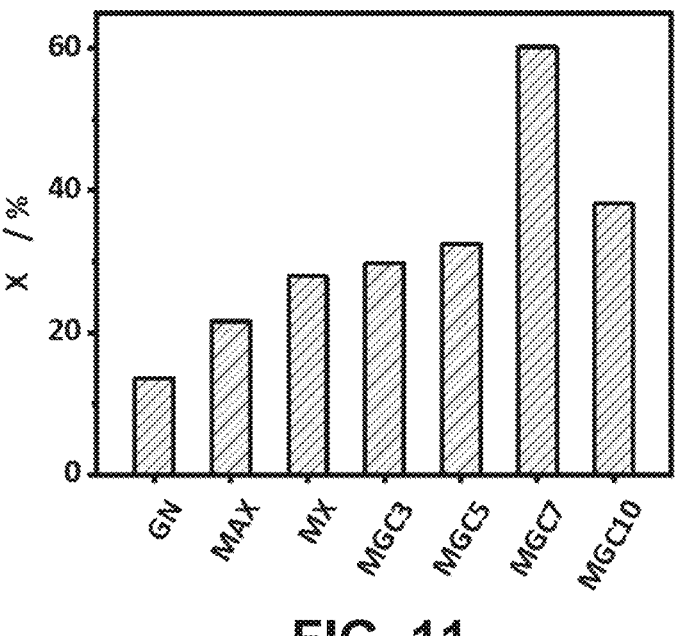
FIG. 11 is a plot of furfural conversion of efficiency of electrodes made with various catalyst compositions, includes samples of a composite catalyst.

The results in Table 2 are shown graphically in FIG. 11.

Figure 12:
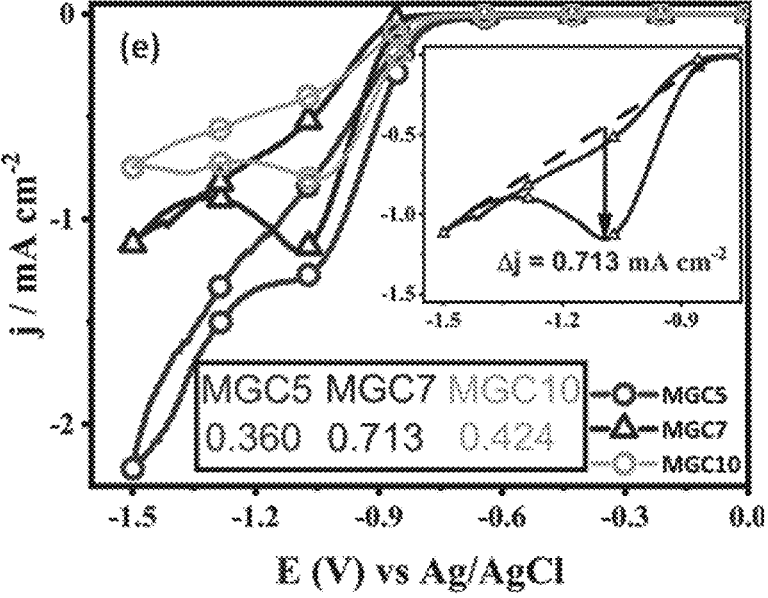
FIG. 12 is a plot of cyclic voltammetry (CV) of the electrodes made with various samples of the composite catalyst.

FIG. 12 shows CV curves for the MGCX samples from Table 1 above (where 'X' is the mass percent of MX in the catalyst composite). The catalysts are immersed in 50 mM FF (labeled with FF, hollow points), 100 mM sulfuric acid and 20 vol % acetonitrile are used. The inset shows the difference ($\Delta j$) between the current density with FF addition in the system and without FF (referred to as blank) such that $\Delta j$=current density without FF minus the current density with FF.

The MGC7 sample is more effective, relatively speaking, in FF reduction. The $\Delta j$ values of FIG. 12 represent the current density of the reduction current. The current density is calculated as 'total current density with FF in the solution minus the current density without FF in the solution.' This provides the current density attributed to FF reduction. Higher current density indicates a higher reduction reaction rate for FF.

FIG. 13 shows the influence of applied potential (100 mM $H_2SO_4$) on FF conversion, selectivity and faradaic efficiency (FE) for the MGC7 catalyst. The solid points depict the applied potential with the best overall results in terms of conversion, selectivity and FE. The data of FIG. 13 is shown in tabular format below.

TABLE 3

Conversion, FE and selectivity as a function of Applied Potential

| Voltage (V vs. Ag/AgCl) | Conversion | F.E. | Selectivity |
|---|---|---|---|
| −0.9 | 52.2 ± 2.2 | 40.3 ± 2.2 | 77.2 ± 2.9 |
| −1.0 | 60.2 ± 3.7 | 46.9 ± 2.3 | 78.0 ± 3.2 |
| −1.1 | 65.5 ± 3.6 | 51.8 ± 3.4 | 79.0 ± 3.1 |
| −1.2 | 62.8 ± 3.5 | 50.0 ± 3.7 | 79.6 ± 2.9 |
| −1.3 | 57.5 ± 2.1 | 45.7 ± 2.6 | 79.4 ± 2.5 |
| −1.4 | 52.8 ± 2.4 | 42.4 ± 2.7 | 80.3 ± 3.7 |
| −1.5 | 44.8 ± 2.2 | 35.9 ± 2.5 | 80.2 ± 3.3 |

FIG. 14 shows the influence of electrolyte molarity (−1.1 VAg/AgCl) on FF conversion, selectivity and faradaic efficiency (FE) for the MGC7 catalyst. Similar to the results in FIG. 13, the solid points depict the molarity with the best overall results in terms of conversion, selectivity and FE. The data of FIG. 14 is shown in tabular format below.

TABLE 4

| Conversion, FE and selectivity as a function of Molarity | | | |
| --- | --- | --- | --- |
| Molarity | Conversion | F.E. | Selectivity |
| 0.1 | 65.5 ± 2.5 | 43.8 ± 1.3 | 66.9 ± 1.7 |
| 0.2 | 81.8 ± 2.1 | 64.2 ± 2.1 | 78.5 ± 2.7 |
| 0.4 | 93.9 ± 3.8 | 83.9 ± 3.1 | 89.4 ± 3.5 |
| 0.6 | 92.5 ± 3.2 | 90.0 ± 3.9 | 96.9 ± 2.7 |
| 0.8 | 95.0 ± 3.9 | 86.8 ± 3.7 | 91.4 ± 3.5 |
| 1.0 | 85.9 ± 3.8 | 71.1 ± 2.6 | 82.7 ± 2.4 |
| 1.2 | 77.6 ± 2.7 | 62.7 ± 2.4 | 80.8 ± 2.3 |
| 1.5 | 70.1 ± 2.6 | 54.1 ± 2.3 | 77.1 ± 2.8 |

In the evaluation under both FIGS. 13 and 14, the catalysts were immersed in 50 mM FF and 20 vol % acetonitrile. The results in FIGS. 13 and 14 demonstrate that FF conversion, MF selectivity and FE can be increased by optimizing parameters such as, for example, voltage and molarity.

ECH Performance Evaluation Equations:

The performance of the ECH of FF were determined using Equations 1, 2 and 3.

$$\text{Reactant Conversion } (X) = \frac{N_i - N_f}{N_i} \times 100 \quad (1)$$

$$\text{Faradaic Efficiency} (F. E.) = \frac{N_{pi} Z F}{Q} \times 100 \quad (2)$$

$$\text{Selectivity } (S) = \frac{N_{pi}}{N_p} \times 100 \quad (3)$$

$N_f$ and Ni represent the final and initial moles of furfural, respectively. Np and Npi represent the total moles of all products and that of the specific product i, respectively. Q, N, and Z represent the total charge passed through the system, Faraday constant, and total number of electrons transferred per molecule of the product, respectively.

Method for Product Identification and Quantification:

At the end of the reaction, samples were taken from the reaction chambers to enable identification of the reaction products. First, the samples were diluted with acetonitrile and filtered with 0.1 μm PTFE syringe filters to remove any particles or impurities that could interfere with the HPLC analysis.

The diluted samples were then analyzed using an Agilent Technologies 1260 HPLC system operating at a detection wavelength of 210 nanometers. This particular wavelength was chosen for its effectiveness in detecting the types of compounds expected in the reaction mixture. The HPLC system was equipped with a high quality column from Phenomenex, Inc., the Gemini C18 model with a particle size of 3 micrometers and a pore size of 110 Angstroms. The HPLC analysis was performed at a controlled temperature of 318 K. A binary gradient method consisting of water and acetonitrile was used for elution. The flow rate of the mobile phase was maintained at 0.6 mL/min to ensure a uniform and consistent flow through the column. The gradient profile for the acetonitrile component was carefully programmed: It started with an initial concentration of 15% (v/v), increased to 75% over a period of 5 to 20 minutes, and then was gradually reduced back to 15% from 20 to 30 minutes.

The products in the samples were identified by comparing their HPLC analysis data with those of standard samples. The standards used for comparison included FF, FA and 2-MF. By matching the retention times and other chromatographic characteristics of the unknown samples with those of the standards, accurate identification of the products formed during the reaction was achieved. Peaks other than those of FF, FA and 2-MF were not quantified and are most likely related to the polymerized FF, which occurs only a few minutes after the retention time of furfural. Complete analysis of polymerized FF would require NMR analysis. The total mass balance was found to be approximately 70-80%.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

Discussion of Possible Embodiments

The following are non-exclusive descriptions of possible embodiments of the present invention.

According to one aspect, a catalyst for electrochemical hydrogenation (ECH) of furfural to 2-methylfuran includes a two-dimensional (2D) multi-layered Molybdenum Mxene; and a two-dimensional (2D) carbon nitride nanosheet. The 2D multi-layered Molybdenum Mxene is dispersed on a surface of the 2D carbon nitride nanosheet.

The catalyst of the preceding paragraph can optionally include, additionally and/or alternatively any, one or more of the following features/steps, configurations and/or additional components.

For example, the Molybdenum Mxene can be Molybdenum carbide.

For example, the Molybdenum Mxene can be Molybdenum nitride.

For example, a mass percent of Molybdenum Mxene in the catalyst can be between about 5 and about 10.

For example, the mass percent of Molybdenum Mxene can be between about 6 and about 8.

For example, the mass percent of Molybdenum Mxene can be about 7.

For example, the carbon nitride nanosheet can be graphitic carbon nitride (g-C$_3$N$_4$).

For example, a mass percent of graphitic carbon nitride in the catalyst can be between about 90 and about 95.

For example, the catalyst is porous and a surface area of the catalyst can be between about 25 m$^2$/g and about 35 m$^2$/g.

For example, the surface area can be about 29 m$^2$/g.

For example, the catalyst is porous and an average pore size of the catalyst can range between about 2 nm and about 6 nm.

For example, the average pore size can range between about 2.8 nm and about 5.2 nm.

For example, the catalyst is thermally stable up to about 340° C.

For example, a faradaic efficiency (FE) of the catalyst is at least 90%.

According to another aspect, a method of making an electrocatalyst for use in electrochemical hydrogenation (ECH) of furfural to 2-methylfuran includes mixing urea, melamine and Molybdenum Mxene to form a mixture. The method further includes heating the mixture to form a two-dimensional (2D)-on-2D composite of Molybdenum Mxene and carbon nitride, and forming the composite into an electrocatalyst powder.

The method of the preceding paragraph can optionally include, additionally and/or alternatively any, one or more of the following features/steps, configurations and/or additional components.

For example, heating the uniform mixture to form the composite can include securing the mixture in a crucible using aluminum sheeting, and placing the crucible in a furnace to heat the mixture and form the composite.

For example, the mixture is gradually heated to a maximum temperature between about 800 and about 830 K.

For example, the maximum temperature is held for about 3 to about 5 hours.

For example, the maximum temperature is held for about 4 hours.

For example, the method can further include making the Molybdenum Mxene prior to mixing urea, melamine and Molybdenum Mxene to form a mixture.

For example, making the Molybdenum Mxene can include mixing MAX phase Molybdenum aluminum carbide with a hydrochloric acid (HCl) solution to form a Mxene mixture.

For example, making the Molybdenum Mxene can include hydrothermally processing the Mxene mixture to form the two-dimensional (2D) multi-layered Molybdenum. For example, a molar ratio of urea to melamine in the mixture is about 1:1.

For example, the Molybdenum Mxene can be Molybdenum carbide.

For example, a mass percent of Molybdenum Mxene in the electrocatalyst powder can be between about 5 and about 10.

For example, the mass percent of Molybdenum Mxene can be between about 6 and about 8.

For example, the Molybdenum Mxene can be Molybdenum nitride.

According to another aspect, a method of producing 2-methylfuran (MF) using a composite catalyst includes directly converting furfural to 2-methylfuran (MF) using an electrochemical reactor and a composite catalyst of 2D Molybdenum Mxene on a carbon nitride nanosheet. The method further includes removing the converted MF from the electrochemical reactor. The composite catalyst has a high selectivity and preference for furfural reduction over a hydrogen evolution reaction (HER).

The method of the preceding paragraph can optionally include, additionally and/or alternatively any, one or more of the following features/steps, configurations and/or additional components.

For example, the electrochemical reactor can be operated as a continuous reactor, and removing the converted MF can comprise continuously collecting vaporized MF in a condenser located on top of the electrochemical reactor.

For example, the electrochemical reactor is operated at about 63° C.

For example, the furfural conversion is at least about 60 percent.

For example, a faradaic efficiency (FE) of the catalyst is at least 90%.

For example, a mass percent of Molybdenum Mxene in the composite catalyst can be between about 5 and about 10.

For example, a mass percent of carbon nitride in the composite catalyst can be between about 90 and about 95.

The invention claimed is:

1. A catalyst for electrochemical hydrogenation (ECH) of furfural to 2-methylfuran, the catalyst comprising:
   a two-dimensional (2D) multi-layered Molybdenum Carbide Mxene; and
   a two-dimensional (2D) carbon nitride nanosheet, wherein the 2D multi-layered Molybdenum Mxene is dispersed on a surface of the 2D carbon nitride nanosheet,
   wherein a mass percentage of the two-dimensional (2D) multi-layered Molybdenum Carbide Mxene in the catalyst ranges from about 5% to about 10%, and wherein an average pore size of the catalyst ranges from about 2 nm to about 6 nm.

2. The catalyst of claim 1, wherein the mass percentage of the two-dimensional (2D) multi-layered Molybdenum Carbide Mxene is about 7.

3. The catalyst of claim 1, wherein the two-dimensional (2D) carbon nitride nanosheet is graphitic carbon nitride $(g\text{-}C_3N_4)$.

4. The catalyst of claim 3, wherein a mass percent of graphitic carbon nitride in the catalyst is between about 90 and about 95.

5. The catalyst of claim 1, wherein the catalyst is thermally stable up to about 340° C.

6. The catalyst of claim 1, wherein the mass percentage of the two-dimensional (2D) multi-layered Molybdenum Carbide Mxene in the catalyst ranges from 6% to 8%.

7. The catalyst of claim 6, wherein the two-dimensional (2D) carbon nitride nanosheet is graphitic carbon nitride $(g\text{-}C_3N_4)$, and wherein the average pore size of the catalyst ranges from 2.8 nm to 5.2 nm.

8. The catalyst of claim 7, wherein the two-dimensional (2D) multi-layered Molybdenum Carbide Mxene is formed without hydrofluoric acid.

9. The catalyst of claim 7, wherein a specific surface area of the catalyst ranges from 25 $m^2$/g to 35 $m^2$/g.

10. The catalyst of claim 1, wherein a specific surface area of the catalyst ranges from 25 $m^2$/g to 35 $m^2$/g.

11. The catalyst of claim 1, wherein a specific surface area of the catalyst ranges from 25 $m^2$/g to 32 $m^2$/g.

* * * * *